United States Patent [19]
Phelps et al.

[11] Patent Number: 5,803,064
[45] Date of Patent: Sep. 8, 1998

[54] ANESTHESIA SYSTEM FOR USE WITH MAGNETIC RESONANCE IMAGING SYSTEMS

[75] Inventors: Robert W. Phelps; Lyle E. Kirson, both of Denver; Kenneth M. Swank, Aurora, all of Colo.

[73] Assignee: University Technology Corporation, Boulder, Colo.

[21] Appl. No.: 909,722

[22] Filed: Aug. 12, 1997

[51] Int. Cl.⁶ .................................................. A61M 16/00
[52] U.S. Cl. ................. 128/203.12; 128/203.28; 128/205.17; 128/205.13; 128/204.18; 128/205.14
[58] Field of Search ......................... 128/203.28, 203.12, 128/205.17, 205.13, 205.11, 204.28, 204.18, 205.14, 205.15, 205.16; 600/411, 420, 309

[56] References Cited

U.S. PATENT DOCUMENTS

| | | | |
|---|---|---|---|
| 733,027 | 7/1903 | Golden | 128/203.25 |
| 4,239,038 | 12/1980 | Holmes | 128/205.13 |
| 4,281,652 | 8/1981 | Miller | 128/204.25 |
| 4,453,543 | 6/1984 | Kφhnke et al. | |
| 4,456,008 | 6/1984 | Clawson et al. | 128/205.19 |
| 4,791,922 | 12/1988 | Lindsay-Scott et al. | 128/205.28 |
| 5,080,093 | 1/1992 | Raabe et al. | 128/203.12 |
| 5,471,979 | 12/1995 | Psaros et al. | |
| 5,485,835 | 1/1996 | Vande Streek et al. | |
| 5,507,280 | 4/1996 | Henkin et al. | |
| 5,520,172 | 5/1996 | Obermayer | |
| 5,522,381 | 6/1996 | Olsson et al. | |
| 5,568,807 | 10/1996 | Mecikalski | |
| 5,619,986 | 4/1997 | Werner et al. | |
| 5,666,946 | 9/1997 | Langenback | 128/200.16 |

*Primary Examiner*—Mickey Yu
*Assistant Examiner*—William J. Deane, Jr.
*Attorney, Agent, or Firm*—Emery L. Tracy; Ruth Eure

[57] ABSTRACT

An anesthesia system for use in MRI suites is provided. The anesthesia system is connected between an anesthesia machine positioned outside the MRI suite and a patient positioned within the MRI suite. The anesthesia machine provides anesthesia gas mixture for anesthetizing the patient. The apparatus has a delivery mechanism for transporting the anesthesia gas mixture from the anesthesia machine to the MRI suite and a mechanism for introducing fresh room air into the anesthesia gas mixture thereby creating a combined gas mixture. A reservoir mechanism receives and stores at least a portion of the anesthesia gas mixture delivered through the delivery mechanism. A mechanism introduces fresh room air into the anesthesia gas mixture thereby creating a combined gas mixture. A ventilation mechanism receives and stores the combined gas mixture. A connector mechanism is mounted to the ventilation mechanism for receiving the combined gas mixture from the ventilation mechanism and a non-rebreathing mechanism inhibits rebreathing of patient exhalation by the patient. A first tube delivers the combined gas mixture from the connector mechanism to the patient and a second tube delivers exhalation from the patient to the non-rebreathing mechanism upon the patient exhaling with the non-breathing mechanism maintaining the patient exhalation from returning to the patient. Finally, a scavenger mechanism associated with the non-rebreathing mechanism releases patient exhalation from the non-rebreathing mechanism to a scavenger system.

22 Claims, 2 Drawing Sheets

ANESTHESIA SYSTEM FOR USE WITH MAGNETIC RESONANCE IMAGING SYSTEMS

BACKGROUND OF THE INVENTION

1. Field of the Invention

This invention relates generally to an anesthesia system and, more particularly, it relates to a magnetic resonance imaging system compatible anesthesia system for providing inhalation agents to a patient undergoing a procedure within a magnetic resonance imaging suite.

2. Description of the Prior Art

During surgery or other procedures, it is often required that the patient be administered an anesthetic, either an intravenous anesthetic or an inhalation anesthetic. In the art, non-rebreathing systems are commercially available which can be attached to a variety of anesthesia machines. Such systems are available in various designs and include the Jackson-Reese, Magill, or Mapelson systems. However, since exhaled gases are not passed through carbon dioxide absorbers, these systems require very high gas flows to eliminate the rebreathing of carbon dioxide. Furthermore, some of the above-identified non-rebreathing systems are not easily adaptable to scavenging or removing waste gases which is essential when inhalation agents are administered. This problem is intensified during magnetic resonance imaging (MRI) where the patient's head is far away (approximately ten (10) to fifteen (15) feet) from the anesthesiologist.

Administration of an inhalation anesthetic for patients undergoing MRI procedures has, until the discovery of the present invention, been limited to those institutions that have access to an MRI-compatible anesthesia delivery system. One example of an MRI-compatible anesthesia delivery system is the EXCEL MRI-Compatible Anesthesia System by Ohmeda (Madison, Wis.). The Ohmeda system is constructed primarily of a non-ferrous material inhibiting attraction to the cryogenic magnets which reside within the MRI systems. Due to the extreme cost of the Ohmeda system, many institutions, either public or private, have not been able to acquire the Ohmeda system. In these instances, anesthesiologists normally provide total intravenous anesthesia (no inhalation agents) for MRI studies that require patients to be under general anesthesia.

Other attempts have been made for providing an anesthesia machine or anesthesia breathing apparatus. The Obermayer, U.S. Pat. No. 5,520,172, describes an anesthetic machine for use as a ventilation part of an anesthesia system having an inspiratory and an expiratory branch. The Obermayer patent attempts to reuse part of the exhaled gas within the patient's exhalation. The Obermayer patent makes no mention of the use of a carbon dioxide absorber although without such a device, the patient would rebreath carbon dioxide. The anesthesia circuit of the present invention does not allow rebreathing of carbon dioxide.

In the Kohnke et al, U.S. Pat. No. 4,453,543, an anesthesia-breathing apparatus is described. Once again, similar to the Obermayer patent, the Kohnke et al patent describes a semi-closed/closed system requiring carbon dioxide absorbers to absorb carbon dioxide prior to rebreathing by the patient. Furthermore, the Kohnke et al patent is not capable of entraining room air if the oxygen line disconnects during use leading to a potentially dangerous situation.

Therefore, it is an object of the present invention to provide an anesthesia system for use with magnetic resonance imaging systems which can be attached to any anesthesia machine.

It is another object of the present invention to provide an anesthesia system for use with magnetic resonance imaging systems which provide a safe inhalation anesthesia at fresh gas flows down to two (2) liters per minute or less without any rebreathing of carbon dioxide by the patient.

It is yet another object of the present invention to provide an anesthesia system for use with magnetic resonance imaging systems which have a ventilation bag positionable at a relatively long distance (fifteen (15) feet or more) from the patient's airway without any difficulty, thereby allowing the anesthesiologist to assist or control ventilation from that remote position.

It is still another object of the present invention to provide a anesthesia system for use with magnetic resonance imaging systems which is easily adaptable for scavenging of all waste gases.

SUMMARY OF THE INVENTION

The present invention is an anesthesia system for use in MRI suites. The anesthesia system of the present invention is connected between an anesthesia machine positioned outside the MRI suite and a patient positioned within the MRI suite. The anesthesia machine provides an anesthesia gas mixture for anesthetizing the patient.

The anesthesia system of the present invention comprises delivery means for transporting the anesthesia gas mixture from the anesthesia machine to the MRI suite and means for introducing fresh room air into the anesthesia gas mixture thereby creating a combined gas mixture. Self-refilling ventilation means receive and store the combined gas mixture, an elbow connector within which is a non-rebreathing means is mounted to the ventilation means and receives the combined gas mixture from the ventilation means. A first tube means delivers the combined gas mixture from the connector to the patient for inhalation consumption by the patient and a second tube means delivers exhalation from the patient to the non-rebreathing means upon the patient exhaling with the non-rebreathing means maintaining the patient exhalation from returning to the patient. Scavenger means associated with the non-rebreathing means releases patient exhalation from the non-rebreathing means to a scavenger system.

In an embodiment of the present invention, the anesthesia system comprises the delivery means being a tube having a predetermined length of up to thirty (30 ft.) feet or greater. Preferably, the tube has a first end and a second end with the first end of the tube being connected to the anesthesia machine.

In another preferred embodiment, the anesthesia system of the present invention comprises a hollow receiving member connectable to the delivery means. The receiving member receives the anesthesia gas mixture from the delivery means and the fresh room air for creating the combined gas mixture.

In yet another preferred embodiment, the anesthesia system of the present invention comprises reservoir means for storing the anesthesia gas mixture prior to entry of the combined gas mixture into the ventilation means. Preferably, the reservoir means has a pressure relief valve for releasing the anesthesia gas mixture from the reservoir means upon attainment of a predetermined pressure within the reservoir means. Furthermore, preferably, the pressure relief valve automatically releases at least a portion of the anesthesia gas mixture from the reservoir means upon attainment of a predetermined pressure.

In still another preferred embodiment, the anesthesia system of the present invention comprises the receiving member being mounted to the ventilation means for delivering the combined gas mixture to the ventilation means. Preferably, a one-way valve is mounted between the ventilation means and the receiving member for providing a flow of the combined gas mixture in a direction into the ventilation means only.

In still yet another preferred embodiment, the anesthesia system of the present invention comprises a one-way valve within the first tube means for delivering the combined gas mixture in a direction toward the patient only. Furthermore, the anesthesia system of the present invention preferably comprises a one-way valve within the second tube means for delivering exhalation from the patient to the non-rebreathing valve in a direction away from the patient only.

The present invention further includes a method for anesthetizing a patient positioned within an MRI suite. The method of the present invention comprises positioning an anesthesia machine outside the MRI suite with the anesthesia machine having a supply of anesthesia gas mixture and delivering the anesthesia gas mixture into the MRI suite. Next, the method comprises storing at least a portion of the anesthesia gas mixture within a reservoir and combining the anesthesia gas mixture stored within the reservoir with fresh room air creating a combined gas mixture. Finally, the method comprises delivering the combined gas mixture to the patient for inhalation by the patient and scavenging any patient exhalation from the patient for removal of the exhalation from rebreathing by the patient.

In an embodiment of the present invention, the method comprises providing ventilation means for receiving and storing the combined gas mixture. Preferably, the method further comprises providing non-rebreathing means for receiving the combined gas mixture from the ventilation means and inhibiting the patient from rebreathing any patient exhalation.

In another embodiment of the present invention, the method comprises providing first tube means for delivering the combined gas mixture from the elbow connector to the patient for inhalation consumption by the patient with the first tube means having a one-way valve within the first tube means for delivering the combined gas mixture in a direction toward the patient only.

In yet another embodiment of the present invention, the method comprises providing second tube means for delivering exhalation from the patient to the non-rebreathing means upon the patient exhaling with the second tube means having a one-way valve within the second tube means for delivering exhalant from the patient in a direction away from the patient only.

In still another embodiment of the present invention, the method comprises providing a hollow receiving member for receiving the anesthesia gas mixture and the fresh room air thereby creating the combined gas mixture.

In still yet another embodiment of the present invention, the method comprises providing the reservoir with a pressure relief valve for releasing the anesthesia gas mixture from the reservoir means upon attainment of a predetermined pressure within the reservoir means.

DETAILED DESCRIPTION OF THE PREFERRED EMBODIMENTS

Figure 1:
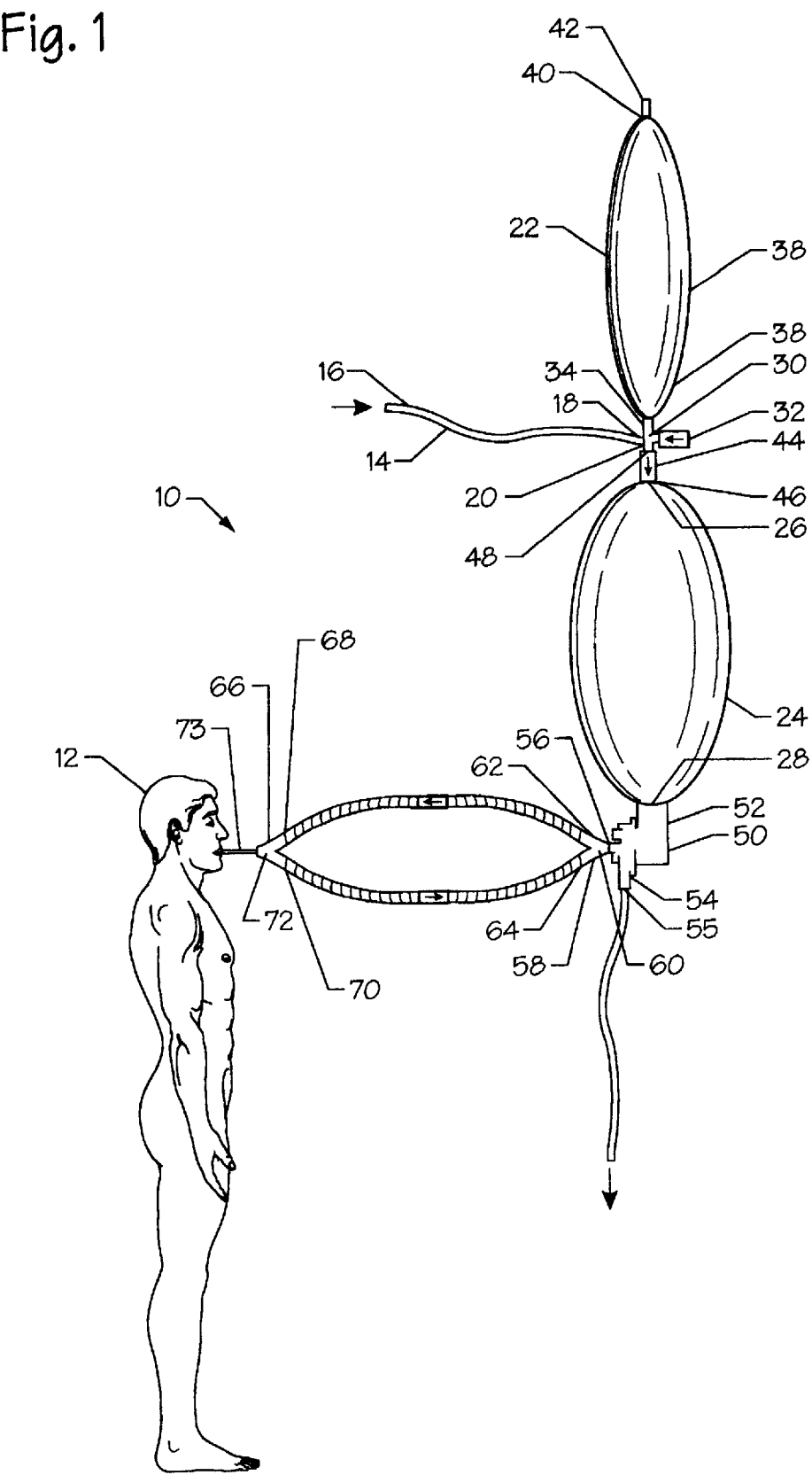
FIG. 1 is an elevational side view illustrating the anesthesia system constructed in accordance with the present invention.

As illustrated in FIG. 1, the present invention is an anesthesia system, indicated generally at 10, for use in magnetic resonance imaging (MRI) suites with MRI systems. The anesthesia system 10 of the present invention is an open system scavenging patient exhalation such that a patient 12 does not rebreath a portion of the gases he or she has already exhaled. Therefore, within the anesthesia system 10 of the present invention, the need for a carbon dioxide absorber is eliminated.

The anesthesia system 10 of the present invention has a gas tube 14 having a first end 16 and a second end 18 opposite the first end 16. The first end 16 of the gas tube 14 is connected to the gas outlet (not shown) of a typical anesthesia machine (not shown) positioned outside the imaging room of the MRI suite. The anesthesia machine stores an anesthesia gas mixture of fresh anesthesia gas and oxygen gas. The anesthesia gas mixture (i.e., oxygen gas and a fresh anesthesia gas) flows from the anesthesia machine and through the gas tube 14. In an alternative embodiment, rather than connecting the first end 16 of the gas tube 14 to the anesthesia machine, it is within the scope of the present invention to have the first end 16 of the gas tube 14 connected to a flow regulator and meter (not shown) of an oxygen outlet within the imaging room and interpositioning an anesthesia vaporizer (not shown) between the flow regulator and meter and the second end 18 of the gas tube 14.

Figure 2:
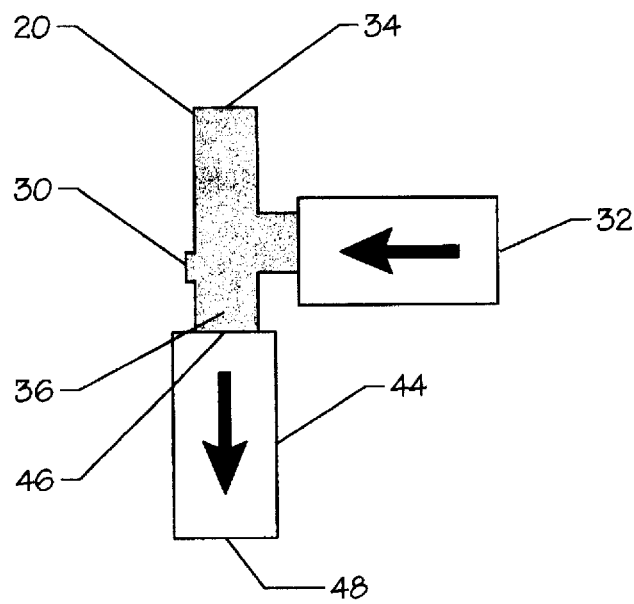
FIG. 2 is a sectional view of a portion of FIG. 1 illustrating the receiving member of the anesthesia system constructed in accordance with the present invention.

As illustrated in FIG. 2, the anesthesia system 10 of the present invention further has a receiving member 20 for receiving the anesthesia gas mixture flow from the gas tube 14, a reservoir bag 22 for receiving the anesthesia gas mixture flow from the receiving member 20, and a self-refilling ventilation bag 24 having a receiving outlet 26 and a discharge outlet 28, the ventilation bag 24 receiving the anesthesia gas mixture flow from the reservoir bag 22 and room air (as will be described below). The receiving member 20 is preferably a hollowed T-piece having a anesthesia gas mixture inlet 30, a room air valve 32, a reservoir outlet 34, and a ventilation outlet 36. The second end 18 of the gas tube 14 is connected to the anesthesia gas mixture inlet 30 for receiving the anesthesia gas mixture flow delivered from the anesthesia machine through the gas tube 14 into the receiving member 20.

The room air valve 32 of the receiving member 20 allows delivery of room air into the ventilation bag 24. The room air valve 32 is preferably a one-way valve allowing room air into the receiving member 20 but not allowing any flow of anesthesia gas mixture or room air from the receiving member 20 and/or the reservoir bag 22 through the room air valve 32 into the MRI suite. Actual operation of the room air valve 32 in conjunction with the other components of the anesthesia system 10 of the present invention will be described in further detail below.

The reservoir bag 22 has a receiving outlet 38 connected to the reservoir outlet 34 of the receiving member 20 with the anesthesia gas mixture flowing from the receiving member 20 through the reservoir outlet 34 to the reservoir bag 22. The reservoir bag 22 further comprises a vented end opening 40 closable by a manual valve 42. The manual valve 42 is normally kept in the closed position, however, if the pressure within the reservoir bag 22 and/or the anesthesia system 10 attains a certain predetermined pressure, the manual valve 42 is manually manipulatable to open the vent end opening 40 releasing the desired amount of pressure within the reservoir bag 22 and the anesthesia system 10. It should be noted, however, that it is within the scope of the present invention to replace the manual valve 42 with an automatic pressure regulated valve (not shown) automatically opening the vented end opening 40 of the reservoir bag 22 when a predetermined pressure is present within the reservoir bag 22 and/or the anesthesia system 10.

The anesthesia system 10 of the present invention also includes a ventilation tube 44 having a first end 46 and a second end 48 substantially opposite the first end 46. The first end 46 of the ventilation tube 44 is connected to the ventilation outlet 36 of the receiving member 20. The second end 48 of the ventilation tube 44 is connected to the receiving outlet 38 of the ventilation bag 24. Similar to the one-way room air valve 32 as described above, the ventilation tube 44 is preferably a one-way valve allowing the combined anesthesia gas mixture from the reservoir bag 22, anesthesia gas mixture from receiving member 20, and room air through the room air valve 32 of the receiving member 20 to flow into the ventilation bag 24 but does not allow any gas flow from the ventilation bag 24 to the receiving member 20.

Figure 3:
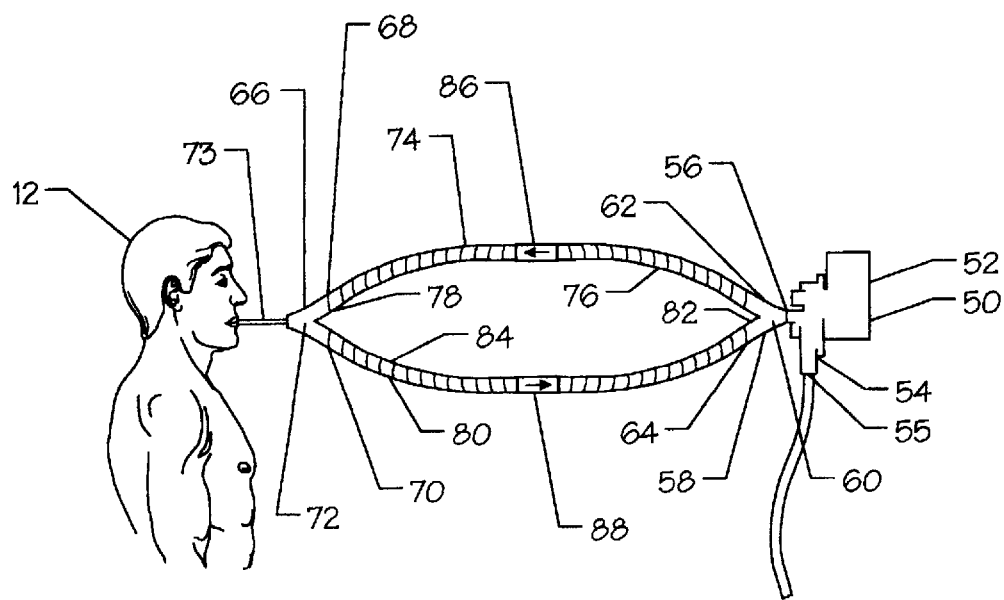
FIG. 3 is a sectional view of FIG. 1 illustrating the elbow connector and inhalation and exhalation tube means of the anesthesia system constructed in accordance with the present invention.

As illustrated in FIG. 3, the anesthesia system 10 of the present invention further has a hollowed elbow connector 50 having a receiving opening 52, a scavenger port 54, and a discharge opening 56. The elbow connector 50 has a non-rebreathing valve (not shown) mounted therein that allows the release of patient exhalation through the scavenger port 54. Examples of valves which can be used for this purpose include, but are not limited to, the Laerdal Anesthesia valve, Lewis-Leigh valve, Ruben valve, or the Stephen-Slater valve. Presence of patient exhalation for discharge through the scavenger port 54 from within the elbow connector 50 will be described in further detail below.

The receiving opening 52 of the elbow connector 50 is connected to the discharge outlet 28 of the ventilation bag 24 for receiving the combined anesthesia gas mixture and room air from the ventilation bag 24. Upon manual compression of the ventilation bag 24, the one-way valve of the ventilation tube 44 inhibits the flow of combined anesthesia gas mixture and room air back into the receiving member 20 and forces the combined anesthesia gas mixture and room air contents of the ventilation bag 24 into the elbow connector 50. When the manual compression on the ventilation bag 24 is released, the ventilation bag 24 self-refills by drawing anesthesia gas mixture from the reservoir bag 22, the receiving member 20, and room air through the one-way room air valve 32 of the receiving member 20. The resulting contents of ventilation bag 24 is a mixture of anesthesia gas mixture from the gas tube 14, anesthesia gas mixture from the reservoir bag 22, and the room air pulled through one-way room air valve 32 of the receiving member 20.

Similar to the one-way room air valve 32 and the one-way ventilation tube 44, a non-rebreathing valve (not shown) of the elbow connector 50 inhibits the contents of the elbow connector 50 and the remaining anesthesia circuit from being drawn back into ventilation bag 24 and subsequently rebreathed by the patient 12. The non-rebreathing valve can be a variety of different designs.

The anesthesia system 10 of the present invention further comprises a hollowed first Y-connector member 58 having a first opening 60, a second opening 62, and a third opening 64 and a second Y-connector member 66 having a first opening 68, a second opening 70, and a third opening 72. The first opening 60 of the first Y-connector member 58 is attached to the discharge outlet 56 of the elbow connector 50 while the third opening 72 of the second Y-connector member 66 is adapted for introduction of the mixed anesthesia gas mixture and room air into the patient 12, i.e. attached to an endotracheal tube 73 inserted into the patient 12, for anesthetizing the patient 12.

A first extension tube 74 having a first end 76 and a second end 78 substantially opposite the first end 76 is provided. The first end 76 of the first extension tube 74 is connected to the second opening 62 of the first Y-connector member 58 and the second end 78 of the first extension tube 74 is connected to the first opening 68 of the second Y-connector member 66. A second extension tube 80 having a first end 82 and a second end 84 substantially opposite the first end 82 is also provided. The first end 82 of the second extension tube 80 is connected to the third opening 64 of the first Y-connector member 58 and the second end 84 of the second extension tube 80 is connected to the second opening 70 of the second Y-connector member 66.

Within each of the first and second extension tubes 74, 80 is a one-way valve 86, 88, respectively. The one-way valve 86 allows the mixed anesthesia gas mixture and room air to flow only in one direction within the first extension tube 74 away from the elbow connector 50 and toward the patient 12 and the one-way valve 88 allows the patient exhalation to flow only in one direction through the second extension tube 80 toward the elbow connector 50 away from the patient 12. Therefore, as the ventilation bag 24 is compressed (i.e., upon inhalation of the patient 12), the contents of the ventilation bag 24 flows through the elbow connector 50, through the first and second openings 60, 62 of the first Y-connector member 58, the one-way valve 86 of the first extension tube 74, and the third and first openings 68, 72 of the second Y-connector member 66 to the patient 12 thereby inflating the patient's lungs. As compression is released on the ventilation bag 24, the non-rebreathing valve in the elbow connector 50 opens to the scavenger port 54 and backflow through elbow connector 50 is inhibited. Therefore, as the patient 12 exhales, the exhaled gas flows through the second and third openings 70, 72 of the second Y-connector member 66, through the one-way valve 88 of the second extension tube 80, through the third and first openings 64, 60 of the first Y-connector member 58, and out the scavenger port 54 of the elbow connector 50 to a typical scavenger system (not shown).

The anesthesia system 10 of the present invention is a breathing circuit which can be connected to an anesthesia gas mixture flow outlet (common gas outlet) of any anesthesia machine. Due to the construction of the typical anesthesia machine from ferrous compounds, the anesthesia machine remains positioned outside the imaging room. When so connected, the anesthesia system 10 allows for the administration of an inhalation anesthesia within the imaging room during MRI studies without the use of a special anesthesia machine or system. The prior art breathing circuits all require high anesthesia gas flows in order to prevent the patient from rebreathing carbon dioxide, and are not generally suitable for scavenging of anesthesia waste gases. Such breathing circuits are truly inappropriate for use in the MRI setting.

Furthermore, the anesthesia system 10 of the present invention comprises a unique design and arrangement of various components which results in an anesthesia circuit with a variety of capabilities not present in the prior art.

These capabilities include delivery of oxygen, air, and inhalation anesthesia, a non-rebreathing circuit, non-rebreathing of patient generated carbon dioxide, low fresh gas flow capability which reduces cost and environmental contamination, positioning of the ventilation bag at a relatively long distance (fifteen (15) feet or more) from the patient airway, and scavenging of waste gases.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

We claim:

1. An anesthesia system for use in MRI suites, the anesthesia system being connected between an anesthesia machine positioned outside the MRI suite and a patient positioned within the MRI suite, the anesthesia machine providing an anesthesia gas mixture for anesthetizing the patient, the apparatus comprising:

delivery means for transporting the anesthesia gas mixture from the anesthesia machine to the MRI suite;

reservoir means for receiving and storing at least a portion of the anesthesia gas mixture delivered through the delivery means;

means for introducing fresh room air into the anesthesia gas mixture thereby creating a combined gas mixture;

ventilation means for receiving and storing the combined gas mixture;

connector means mounted to the ventilation means for receiving the combined gas mixture from the ventilation means;

non-rebreathing means for inhibiting rebreathing of patient exhalation by the patient;

first tube means for delivering the combined gas mixture from the connector means to the patient for inhalation consumption by the patient; and second tube means for delivering exhalation from the patient to the non-rebreathing means upon the patient exhaling, the non-breathing means maintaining the patient exhalation from returning to the patient; and scavenger means associated with the non-rebreathing means for releasing patient exhalation from the non-rebreathing means to a scavenger system.

2. The system as claimed in claim 1 wherein the delivery means is a tube having a predetermined length, the tube having a first end and a second end, the first end of the tube being connected to the anesthesia machine.

3. The system as claimed in claim 2 wherein the tube has a length up to and including approximately thirty (30 ft.) feet.

4. The system as claimed in claim 1 and further comprising a hollow receiving member connectable to the delivery means, the receiving member receiving the anesthesia gas mixture from the delivery means and the fresh room air for creating the combined gas mixture.

5. The system as claimed in claim 1 wherein the reservoir means has a pressure relief valve for releasing the anesthesia gas mixture from the reservoir means upon attainment of a predetermined pressure within the reservoir means.

6. The system as claimed in claim 5 wherein the pressure relief valve automatically releases at least a portion of the anesthesia gas mixture from the reservoir means upon attainment of a predetermined pressure.

7. The system as claimed in claim 4 wherein the receiving member is mounted to the ventilation means for delivering the combined gas mixture to the ventilation means, and further comprising a one-way valve mounted between the ventilation means and the receiving member for providing a flow of the combined gas mixture in a direction into the ventilation means only.

8. The system as claimed in claim 1 and further comprising a one-way valve within the first tube means for delivering the combined gas mixture in a direction toward the patient only.

9. The system as claimed in claim 1 and further comprising a one-way valve within the second tube means for delivering exhalation from the patient to the non-rebreathing means in a direction away from the patient only.

10. The system as claimed in claim 1 wherein the non-rebreathing means is mounted within the connector means inhibiting rebreathing of patient exhalation by the patient.

11. An anesthesia system connected between an anesthesia machine positioned outside an MRI suite and a patient positioned within the MRI suite, the anesthesia machine providing anesthesia gas mixture, the apparatus comprising:

a fresh gas tube having a first end and a second end, the first end mountable to the anesthesia machine for carrying anesthesia gas mixture from the anesthesia machine into the MRI suite;

a hollow receiving member mounted to the second end of the fresh gas tube, the receiving member having a reservoir outlet, a one-way air inlet for receiving room air into the hollow receiving member, and a one-way ventilation outlet for dispensing room air and the anesthesia gas mixture from the receiving member and an anesthesia gas mixture inlet for receiving the anesthesia gas mixture from the fresh gas tube;

a reservoir bag mounted to the reservoir outlet for receiving the anesthesia gas mixture from the fresh gas tube;

a ventilation bag mounted to the ventilation outlet for receiving the combined room air and the anesthesia gas mixture from the receiving member and the reservoir bag, the ventilation bag having an outlet formed therein;

a connector mechanism mounted to the outlet of the ventilation bag, the connector mechanism receiving the combined room air and the anesthesia gas mixture from the ventilation bag;

a non-rebreathing valve to inhibit rebreathing of patient exhalation by the patient;

a first ventilation tube for delivering the combined room air and the anesthesia gas mixture from the non-rebreathing valve to the patient, the first ventilation tube maintaining the combined room air and the anesthesia gas mixture flow in a direction toward the patient and away from the connector means; and a second ventilation tube for delivering exhalation from the patient to the non-rebreathing valve, the second ventilation tube maintaining the exhalation flow in a direction toward the non-rebreathing valve and away from the patient;

wherein the non-rebreathing valve has a scavenger outlet for dispersing patient exhalation from the non-rebreathing valve away from the patient.

12. The apparatus as claimed in claim 11 and further comprising a one-way valve mounted within the first ventilation tube for delivering the room air and the anesthesia gas mixture in a direction toward the patient only.

13. The apparatus as claimed in claim 11 and further comprising a one-way valve mounted within the second tube means for delivering exhalation from the patient to the non-rebreathing valve in a direction away from the patient only.

14. The apparatus as claimed in claim 11 wherein the reservoir bag has a pressure relief valve for releasing the combined gas mixture from the reservoir bag upon attainment of a predetermined pressure within the reservoir means.

15. The apparatus as claimed in claim 11 wherein the non-rebreathing means is positioned within the connector means.

16. A method for anesthetizing a patient positioned within an MRI suite, the method comprising:

positioning an anesthesia machine outside the MRI suite, the anesthesia machine having a supply of anesthesia gas mixture;

delivering the anesthesia gas mixture into the MRI suite;

storing at least a portion of the anesthesia gas mixture within a reservoir;

combining the anesthesia gas mixture stored within the reservoir with fresh room air creating a combined gas mixture;

delivering the combined gas mixture to the patient for inhalation by the patient; and scavenging any patient exhalation from the patient for removal of the exhalation from rebreathing by the patient.

17. The method as claimed in claim 16 and further comprising providing ventilation means for receiving and storing the combined gas mixture.

18. The method as claimed in claim 17 and further comprising providing non-rebreathing means for receiving the combined gas mixture from the ventilation means and inhibiting the patient from rebreathing any patient exhalation.

19. The method as claimed in claim 16 and further comprising providing first tube means for delivering the combined gas mixture from the non-rebreathing means to the patient for inhalation consumption by the patient, the first tube means having a one-way valve within the first tube means for delivering the combined gas mixture in a direction toward the patient only.

20. The method as claimed in claim 16 and further comprising providing second tube means for delivering exhalation from the patient to the non-rebreathing means upon the patient exhaling, the second tube means having a one-way valve within the second tube means for delivering exhalant from the patient in a direction away from the patient only.

21. The method as claimed in claim 16 and further comprising providing a hollow receiving member for receiving the anesthesia gas mixture and the fresh room air thereby creating the combined gas mixture.

22. The method as claimed in claim 16 and further comprising providing the reservoir with a pressure relief valve for releasing the anesthesia gas mixture from the reservoir means upon attainment of a predetermined pressure within the reservoir means.

* * * * *